United States Patent [19]

McCurry, Jr. et al.

[11] Patent Number: 5,478,930
[45] Date of Patent: Dec. 26, 1995

[54] PROCESS FOR PRODUCING LIGHT COLORED ALKYL POLYGLUCOSIDES WITH PARTIALLY SULFATED FATTY ALCOHOL CATALYSTS

[75] Inventors: Patrick M. McCurry, Jr., Lansdale, Pa.; Rainer Eskuchen, Langenfeld; Paul Schulz, Wuppertal, both of Germany

[73] Assignee: Henkel Kommanditgesellschaft auf Aktien, Duesseldorf, Germany

[21] Appl. No.: 288,409

[22] Filed: Aug. 10, 1994

Related U.S. Application Data

[63] Continuation of Ser. No. 124,121, Sep. 20, 1993, abandoned.

[51] Int. Cl.$^6$ .......................... C07H 15/04; C07H 15/10; C07H 1/00
[52] U.S. Cl. ...................... 536/18.6; 536/4.1; 252/174.17
[58] Field of Search ................................. 536/4.1, 18.6; 252/174.17

[56] References Cited

U.S. PATENT DOCUMENTS

| 4,885,379 | 12/1989 | Abend | 558/34 |
| 4,973,686 | 11/1990 | Kretschmann et al. | 536/118 |
| 4,977,253 | 12/1990 | Ripke | 536/118 |
| 5,003,057 | 3/1991 | McCurry et al. | 536/18.6 |
| 5,037,992 | 8/1991 | Ward et al. | 558/36 |

FOREIGN PATENT DOCUMENTS

| 0132043 | 1/1985 | European Pat. Off. . |
| 0132046 | 4/1988 | European Pat. Off. . |
| 0301298 | 2/1989 | European Pat. Off. . |
| 0415192 | 3/1991 | European Pat. Off. . |
| 9003977 | 4/1990 | WIPO . |

OTHER PUBLICATIONS

SOFW—Journal, Branca, "Development and Trends of Sugar Derived Surfactants", 1992.
SOFW—Journal, Ripke, "Alkylpolyglucoside—Herstellung und Anwendung (Production and Application," 1992—Abstract–Only.

Primary Examiner—David M. Naff
Assistant Examiner—Francisco C. Prats
Attorney, Agent, or Firm—Ernest G. Szoke; Wayne C. Jaeschke; John E. Drach

[57] ABSTRACT

Light-colored alkyl or alkenyl oligoglucosides are obtained by a process in which glucose or aqueous starch degradation products are reacted with fatty alcohols in the presence of acidic catalysts which are obtained by partial sulfation of $C_{4-22}$ fatty alcohols.

2 Claims, No Drawings

PROCESS FOR PRODUCING LIGHT COLORED ALKYL POLYGLUCOSIDES WITH PARTIALLY SULFATED FATTY ALCOHOL CATALYSTS

This application is a continuation of application Ser. No. 08/124,121 filed on Sep. 20 1993, now abandoned.

BACKGROUND OF THE INVENTION

1. Field of the Invention

This invention relates to a process for the production of light colored alkyl or alkenyl polyglucosides.

2. Description of the Related Art

Alkyl oligoglycosides, more particularly alkyl oligoglucosides, are nonionic surfactants which are acquiring increasing significance by virtue of their excellent detergent properties and their high ecotoxicological compatibility. They are normally produced from glucose which is acetalized with fatty alcohols in the presence of acidic catalysts. The catalyst is then neutralized, excess fatty alcohol is removed and the product is bleached.

Basically, acids are used as catalysts for the acetalization. Sulfuric acid, for example, is extremely effective in the condensation, but always leads to very dark-colored products which are difficult or impossible to lighten. In addition, a high content of unwanted secondary products, particularly polyglucose, is observed. In the past, there has been no shortage of proposals for suitable acidic catalysts. For example, p-toluene sulfonic acid and, in particular, anionic surfactants in acidic form, for example long-chain alkylbenzene sulfonic acids, sulfosuccinic acid, alkyl sulfonic acids and sulfuric acid halfesters of fatty alcohols and polyglycol ethers thereof, have been used as catalysts. Unfortunately, all these known processes are attended by the disadvantage that, even after bleaching, the color quality of the resulting alkyl oligoglucosides is not entirely satisfactory. Even in regard to the secondary products, there is a need for substances of reduced polyglucose content. The use of surface-active catalysts leads to intensive foaming during the reaction. Finally, the use of petrochemical catalysts with an aromatic ring structure in alkyl oligoglucosides otherwise based solely on natural raw materials is often undesirable for fundamental reasons.

Accordingly, the cumulative problem addressed by the present invention was to provide an improved process for the production of light-colored alkyl and/or alkenyl oligoglycosides which would be free from the disadvantages mentioned above.

SUMMARY OF THE INVENTION

A process has surprisingly been discovered that utilizes a partly sulfated fatty alcohol as a catalyst in the acetalization reaction of glucose to yield alkyl polyglucosides in high yields which, after bleaching, are lighter in color and contain less secondary products, particularly polyglucose, than products which have been produced using conventional catalysts. The process comprises reacting glucose or aqueous starch degradation products with a fatty alcohol in the presence of an acidic catalyst which is obtained by partial sulfation of a fatty alcohol of the formula (I)

$$R^1\text{—OH} \qquad (I)$$

wherein $R^1$ is an alkyl or alkenyl radical having from 4 to 22 carbon atoms, and wherein the degree of sulfation is from 1 to 50% of the theoretical value. Any increase in the degree of sulfation beyond 50% of the theoretical value leads to an increase in the secondary products and to a deterioration in color quality.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

Catalysts according to the invention are partial reaction products of saturated and/or unsaturated fatty alcohols with sulfating agents, such as oleum, chlorosulfonic acid or, in particular, gaseous sulfur trioxide.

Examples of suitable catalysts are the partial sulfation products of butanol, caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol and erucyl alcohol and technical mixtures thereof such as are formed, for example, in the high-pressure hydrogenation of fatty acid methyl esters or aldehydes from Roelen's oxo synthesis.

Fatty alcohols containing 8 to 16 carbon atoms, for example technical coconut oil or palm kernel oil fatty alcohols, are preferably used. In one preferred embodiment of the invention, acidic sulfation products of fatty alcohols which coincide in their chain length with the alkyl and/or alkenyl radical of the glucoside are used as catalysts.

A critical parameter for the process according to the invention is the degree of sulfation of the catalysts which is between 1 and 50% of the theoretical and preferably between 10 and 30% of the theoretical. However, since the degree of sulfation and the molar ratio of fatty alcohol to sulfating agent correspond with sufficient accuracy in the particular range required, the degree of sulfation may be adjusted through this parameter. Plant-specific optimization can be routinely carried out by the expert without requiring any inventive activity. The partial sulfation products may normally be prepared by reaction of the fatty alcohols with $SO_3$ in a molar ratio of 1:0.01 to 1:0.5 and preferably in a molar ratio of 1:0.1 to 1:0.3 at temperatures in the range from 25° to 50° C. and preferably at temperatures in the range from 30° to 40° C.

The acidic catalysts may be used in typical quantities of 0.1 to 5% by weight and preferably 0.3 to 1% by weight, based on glucose. The term "acidic catalyst" includes sulfated and non-sulfated product. After conversion, 0.002 to 0.05 and preferably 0.005 to 0.02 mol sulfur trioxide may be used per mole of glucose.

Besides anhydrous glucose, suitable sugar components are glucose monohydrate and aqueous starch degradation products or powders thereof obtained by drying. Starch degradation products are understood to be aqueous glucose or dextrose sirups having a solids content of 70 to 90% by weight and a DP1 degree (monoglucose content) of 80 to 99% by weight.

Suitable fatty alcohols are $C_{6-22}$ and preferably $C_{8-16}$ fatty alcohols. Technical $C_{12-16}$ fatty alcohols or $C_{8-10}$ fatty alcohols based on coconut oil or palm kernel oil are preferably used.

After the acetalization, the acidic catalysts may be neutralized in known manner, more particularly by the addition of magnesium oxide and/or sodium hydroxide solution. The excess fatty alcohol is best removed in two stages by rough depletion in a falling-film evaporator and fine depletion in a thin-layer evaporator. The resulting alkyl and/or alkenyl oligoglycosides may then be made into a paste with water and/or bleached with hydrogen peroxide.

EXAMPLE 1

Sulfation Procedure

About 193 g (1 mol) technical $C_{12/14}$ coconut oil fatty alcohol (Lorol® Spezial, hydroxyl value 290, a product of Henkel KGaA, Düsseldorf, FRG) were introduced into a 1 liter sulfation reactor equipped with jacket cooling and a gas inlet pipe and reacted at 30° C. with 0.1 to 0.95 mol gaseous sulfur trioxide. The $SO_3$ was driven out by heating from a corresponding quantity of 65% oleum, diluted to a concentration of 3% by volume and introduced into the fatty alcohol over a period of 30 minutes. The characteristic data of the product are set out in Table 1.

TABLE 1

Fatty alcohol sulfuric acid semiesters

| Ex. | $SO_3$ quantity mol | Anionic surfactant content* % by weight | Degree of sulfation % of the theoretical |
| --- | --- | --- | --- |
| H1 | 0.1 | 8 | 9 |
| H2 | 0.2 | 17 | 16 |
| H3 | 0.3 | 22 | 21 |
| H4 | 0.4 | 45 | 44 |
| H5 | 0.95 | 94 | 92 |

*To determine the anionic surfactant content, the acidic sulfation products were neutralized and then further treated by DGF-Einheitsmethode H-III-10, Stuttgart 1950–1984. The figure is based on 100% by weight solids.

EXAMPLE 2

Preparation of an Alkyl Polyglucoside

About 234 g (1.3 mol) anhydrous glucose were introduced into a 1 liter three-necked flask equipped with a stirrer, dropping funnel and distillation column, followed by the addition of 1400 g (6.5 mol) $C_{12/14}$ coconut oil fatty alcohol (Lorol® Spezial, hydroxyl value: 290; a product of Henkel KGaA, Düsseldorf, FRG). The reaction mixture was preheated to 90° C., a vacuum of 20 mbar was applied and quantities of 0.2% by weight, based on glucose and on the particular sulfur trioxide content, of catalysts H1 to H4 according to the invention and comparison catalysts H5, X and Y were then introduced over periods of 5 minutes through the dropping funnel. After the additions, the reaction mixture was heated to 105° C. until no more water of condensation could be distilled off. The crude reaction product was neutralized, transferred to a vacuum distillation apparatus and the excess fatty alcohol was distilled off at a temperature of 180° C. and under a reduced pressure of 5 mbar. The products were then bleached with 1% by weight hydrogen peroxide, based on the products, at pH 9. The results are set out in Table 2.

TABLE 2

Characteristic data of the products

| Ex. | Catalyst | Color Gardner | c(PG) % by weight |
| --- | --- | --- | --- |
| 1 | H1 | 3 | 3.4 |
| 2 | H2 | <2 | 3.2 |
| 3 | H3 | 2 | 3.6 |
| 4 | H4 | 3 | 4.8 |
| C1 | H5 | 4 | 5.0 |
| C3 | X | 4 | 5.5 |
| C4 | Y | 4 | 5.3 |

Legend:
c(PG) = Concentration of polyglucose
X = p-Toluene sulfonic acid
Y = Sulfosuccinic acid

What is claimed is:

1. A process for preparing an alkyl polyglucoside which comprises reacting glucose with a first $C_{8-22}$ fatty alcohol in the presence of an acidic catalyst wherein said catalyst is obtained by partial sulfation with sulfur trioxide of a second fatty alcohol of the formula (I)

$$R^1\text{—OH} \qquad (I)$$

wherein $R^1$ is an alkyl or alkenyl radical having from 8 to 22 carbon atoms, wherein the degree of sulfation is from 10 to 30% of the theoretical value and the amount of the catalyst is from about 0.1 to about 5% by weight of glucose.

2. The process of claim 1 wherein the glucose is provided as a water containing starch degradation product having a total solids content of 70 to 90% by weight and a DP1 degree of 80 to 99% by weight.

* * * * *